US008701668B2

(12) United States Patent
Selvarajan et al.

(10) Patent No.: US 8,701,668 B2
(45) Date of Patent: Apr. 22, 2014

(54) NASAL ASSEMBLY

(75) Inventors: Karthikeyan Selvarajan, Gosford (AU);
Philip Rodney Kwok, Chatswood (AU);
Philip John Gunning, North Rocks
(AU)

(73) Assignee: ResMed Limited, Bella Vista (AU)

( * ) Notice: Subject to any disclaimer, the term of this patent is extended or adjusted under 35 U.S.C. 154(b) by 1828 days.

(21) Appl. No.: 11/988,928

(22) PCT Filed: Oct. 12, 2006

(86) PCT No.: PCT/AU2006/001494
§ 371 (c)(1),
(2), (4) Date: Jan. 17, 2008

(87) PCT Pub. No.: WO2007/041786
PCT Pub. Date: Apr. 19, 2007

(65) Prior Publication Data
US 2010/0132716 A1    Jun. 3, 2010

Related U.S. Application Data

(60) Provisional application No. 60/726,182, filed on Oct. 14, 2005.

(51) Int. Cl.
*A61M 11/00*    (2006.01)
(52) U.S. Cl.
USPC .................... 128/207.18; 128/207.13
(58) Field of Classification Search
USPC ............. 128/207.18, 848, 202.27, 204.18,
128/205.25, 206.21, 206.24, 207.13
See application file for complete search history.

(56) References Cited

U.S. PATENT DOCUMENTS

| 4,535,767 | A | 8/1985 | Tiep et al. |
| 4,782,832 | A | 11/1988 | Trimble et al. |
| 6,431,172 | B1 | 8/2002 | Bordewick |
| 6,478,026 | B1 * | 11/2002 | Wood ........................ 128/207.18 |
| 7,318,437 | B2 | 1/2008 | Gunaratnam et al. |
| 7,461,656 | B2 | 12/2008 | Gunaratnam et al. |
| 7,874,293 | B2 | 1/2011 | Gunaratnam et al. |
| 7,900,635 | B2 | 3/2011 | Gunaratnam et al. |
| 8,042,546 | B2 | 10/2011 | Gunaratnam et al. |
| 8,186,352 | B2 | 5/2012 | Gunaratnam et al. |
| 2002/0043265 | A1 * | 4/2002 | Barnett et al. ........... 128/206.24 |

(Continued)

FOREIGN PATENT DOCUMENTS

| WO | 2004/073778 | 9/2004 |
| WO | 2005/016402 | 2/2005 |

(Continued)

OTHER PUBLICATIONS

International Search Report for PCT/AU2006/001494 mailed Nov. 17, 2006.

*Primary Examiner* — Steven Douglas
(74) *Attorney, Agent, or Firm* — Nixon & Vanderhye P.C.

(57) ABSTRACT

A nasal assembly includes a patient interface including a hollow body that defines an air chamber and a pair of nozzles supported by the hollow body. Each nozzle includes a conical tip structured to sealingly communicate with a respective nasal passage of a patient's nose in use. Headgear is provided to the patient interface so as to maintain the patient interface in a desired position on the patient's face in use. The hollow body is bendable to adjust a position of the nozzles in use.

35 Claims, 7 Drawing Sheets

(56) References Cited

U.S. PATENT DOCUMENTS

| | | |
|---|---|---|
| 2003/0196655 A1* | 10/2003 | Ging et al. .............. 128/201.22 |
| 2004/0020493 A1 | 2/2004 | Wood |
| 2004/0025885 A1* | 2/2004 | Payne, Jr. ...................... 128/848 |
| 2004/0226566 A1 | 11/2004 | Gunaratnam et al. |
| 2005/0028821 A1 | 2/2005 | Wood et al. |
| 2005/0028823 A1 | 2/2005 | Wood |
| 2005/0061326 A1 | 3/2005 | Payne, Jr. |
| 2005/0241644 A1 | 11/2005 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2011/0162655 A1 | 7/2011 | Gunaratnam et al. |

FOREIGN PATENT DOCUMENTS

| | | |
|---|---|---|
| WO | 2005/063328 | 7/2005 |
| WO | 2005/097247 | 10/2005 |
| WO | 2005/099801 | 10/2005 |

* cited by examiner

NASAL ASSEMBLY

CROSS REFERENCE TO APPLICATIONS

This application is the U.S. National Phase of International Application No. PCT/AU2006/001494 filed Oct. 12, 2006 and claims the benefit of U.S. Provisional Application No. 60/726,182, filed Oct. 14, 2005, the entire contents of each of which is incorporated herein by reference in its entirety.

FIELD OF THE INVENTION

The present invention relates to a nasal assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

Some nasal assemblies used in the treatment of SDB are designed for insertion into the nasal passages of the patient. Air or other breathable gas is supplied by a blower and passed along a flexible conduit to the nasal assembly.

The nasal assembly generally includes a relatively rigid shell, e.g., a frame, and a pair of nozzles (which may be in the form of nasal pillows, nasal prongs, cannula, or nasal puffs) that are mounted on the rigid shell and structured to be inserted into the nasal passages of the patient. The nozzles are usually held in place using a headgear assembly, the relatively rigid shell and headgear assembly being joined using some form of connector.

A key factor in the efficacy of therapy and compliance of patients with therapy is the comfort and fit of the nasal assembly. While there are a large number of nasal assemblies designed for adults, there are relatively few designed to suit children.

SUMMARY OF THE INVENTION

One aspect of the present invention relates to a nasal assembly suitable for children or pre-adults.

Another aspect of the present invention relates to a nasal assembly that provides comfort and softness, stability, and/or unobtrusiveness.

Another aspect of the present invention relates to a nasal assembly including a patient interface including a hollow body that defines an air chamber and a pair of nozzles supported by the hollow body. Each nozzle includes a conical tip structured to sealingly communicate with a respective nasal passage of a patient's nose in use. Headgear is provided to the patient interface so as to maintain the patient interface in a desired position on the patient's face in use. The hollow body is bendable to adjust a position of the nozzles in use.

Yet another aspect of the present invention relates to a nasal assembly including a tubular air chamber that provides at least one lateral inlet and a pair of nozzles supported by the tubular air chamber. Each nozzle includes a conical tip structured to sealingly communicate with a respective nasal passage of a patient's nose in use. The conical tip includes an outlet opening. The outlet opening has a circular shape.

Still another aspect of the present invention relates to a nasal assembly including a patient interface including a hollow body that defines an air chamber and a pair of nozzles supported by the hollow body. Each nozzle includes a conical tip structured to sealingly communicate with a respective nasal passage of a patient's nose in use. Headgear is provided to the patient interface so as to maintain the patient interface in a desired position on the patient's face in use. The patient interface contacts the patient's face only at the nose and below the nose in use.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
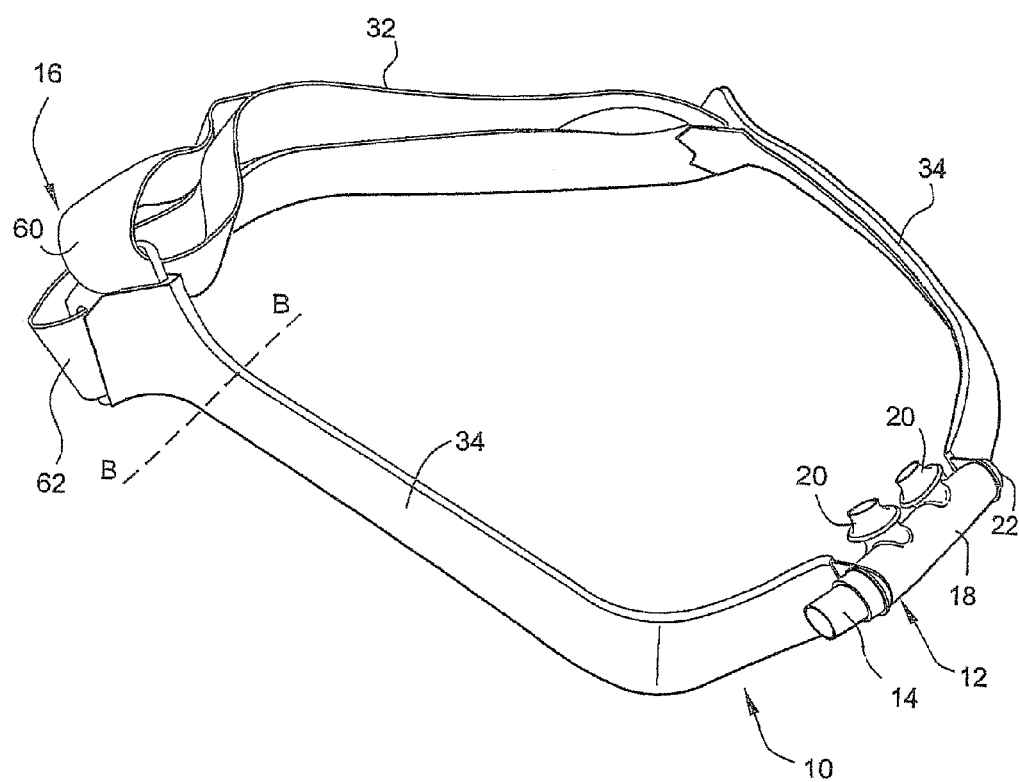
FIG. 1 is a perspective view of a nasal assembly according to an embodiment of the present invention.

FIG. 1 illustrates a nasal assembly 10 according to an embodiment of the present invention. As illustrated, the nasal assembly 10 includes a patient interface 12 that provides an effective seal with the patient's nasal passages, an air delivery connecting member 14, e.g., elbow, provided to one end of the patient interface 12 to deliver breathable gas into the patient interface 12 for breathing by the patient, and headgear 16 provided to the patient interface 12 so as to maintain the patient interface 12 in a desired position on the patient's face.

The overall architecture of the nasal assembly 10 is similar to the nasal assembly disclosed in U.S. patent application Ser. No. 10/781,929, filed Feb. 20, 2004, and Ser. No. 11/101,657, filed Apr. 8, 2005, the entireties of both being incorporated herein by reference. In contrast, the nasal assembly 10 is modified in size and shape for children or pre-adults in the range of 2-3 years old. However, the nasal assembly 10 may be designed for children or pre-adults in the range of 2-12 years old. Also, aspects of the present invention may be applicable to other breathing arrangements and other age groups.

1. Patient Interface

Figure 2:
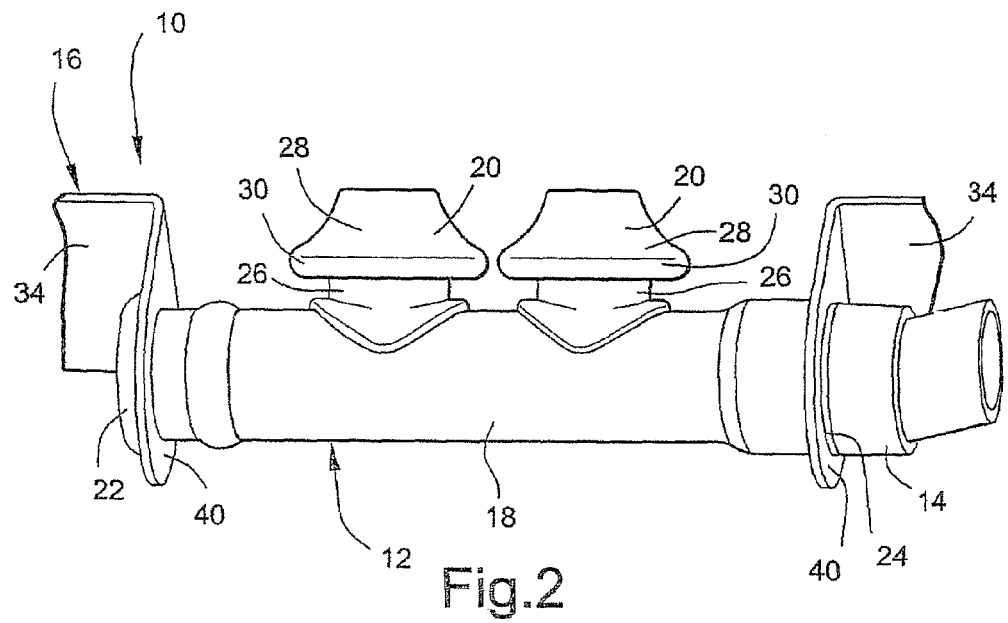
FIG. 2 is a front perspective view of the patient interface of the nasal, assembly shown in FIG. 1.
Figure 3:
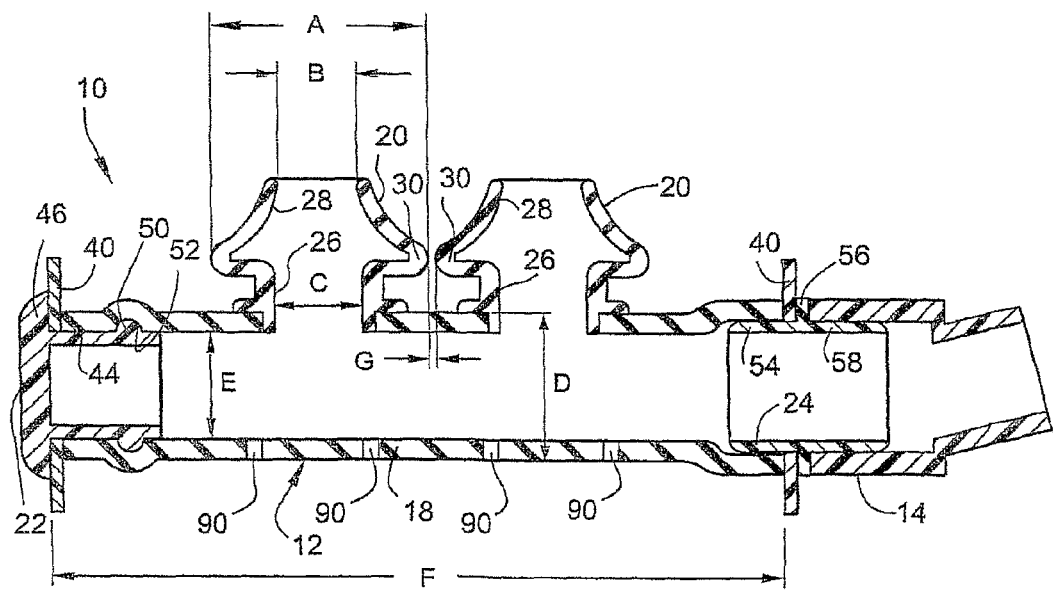
FIG. 3 is a cross-sectional view of the patient interface shown in FIG. 2.

As best shown in FIGS. 2 and 3, the patient interface 12 includes a hollow body or barrel 18 that defines an air chamber and a pair of nozzles 20 supported by the hollow body 18. In an embodiment, the hollow body 18 and nozzles 20 may be formed separately from one another, e.g., by silicone in an injection molding process, and then attached to one another. However, the hollow body 18 and nozzles 20 may formed as a one-piece structure such that the hollow body 18 is integrally formed in one-piece along with the nozzles 20, e.g., by silicone in an injection molding process.

1.1 Hollow Body

The hollow body or barrel 18 is in the form of a silicone cylindrical tube. In the illustrated embodiment, one end of the hollow body 18 is provided with a plug 22 and the other end is provided with a connector or retainer 24 that supports the air delivery connecting member 14. The positions of the plug 22 and connector 24 may be interchanged, according to preference, e.g., the typical sleeping position of the patient. One or more vents 90, e.g., four vent openings with 2 mm diameters, may be provided in the hollow body 18 for $CO_2$ washout (see FIG. 3). In the illustrated embodiment, the vents 90 are provided on a side of the hollow body 18 opposite the nozzles 20. However, other vent arrangements are possible.

1.2 Nozzles

Each nozzle 20 is in the form of a nasal prong and includes a cylindrical tube portion 26 provided to the hollow body 18 and a conical tip 28 structured to sealingly communicate with a respective nasal passage of a patient's nose in use. Each conical tip 28 has a generally cone-like shape with a flange or widened portion 30. However, the nozzles 20 may have other suitable forms to sealingly communicate with the patient's nasal passages, e.g., nasal pillows, cannula, nasal puffs.

Figure 4:
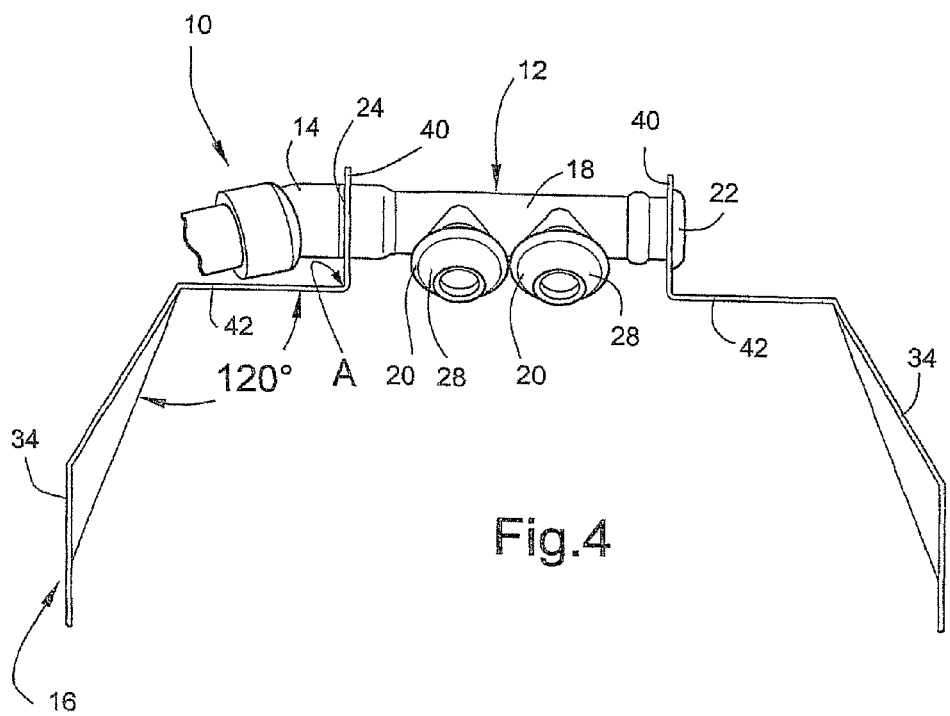
FIG. 4 is a rear perspective view of the nasal assembly shown in FIG. 1 and showing exemplary dimensions of an embodiment.
Figure 5:
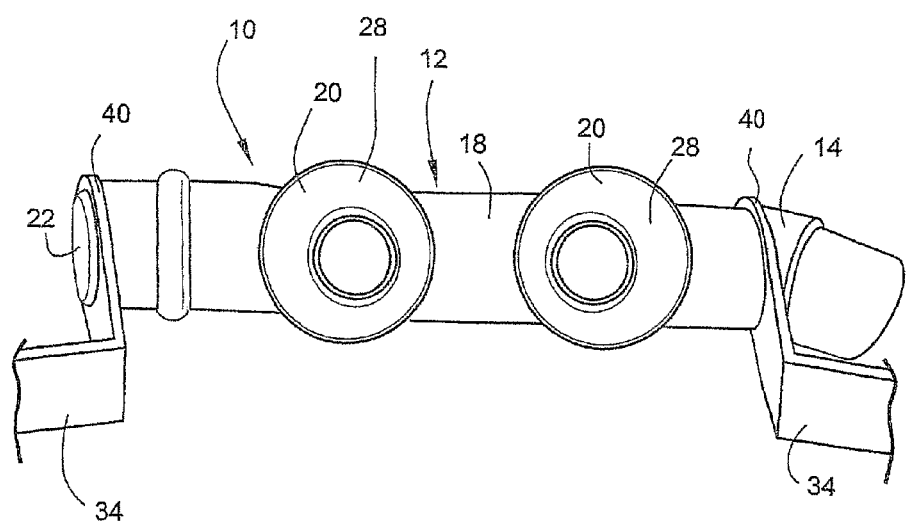
FIG. 5 is an enlarged top view of the patient interface of the nasal assembly shown in FIG. 1.

As best shown in FIGS. 4 and 5, each conical tip 28 is substantially circular in plan view to conform to a child's nasal passages and ensure substantially even loading into a child's nose. This arrangement dictates that the tube portion 26 is also circular in shape so that the load is transferred evenly to the conical tip 28.

In the illustrated embodiment, the nozzles 20 extend out from the hollow body 18 in parallel relation (see FIGS. 2 and 3). However, the nozzles 20 may be angled with respect to the hollow body 18 to properly position the nozzles with respect to the nasal passages of the patient. Also, a space G is provided between the nozzles 20 to accommodate the patient's septum. As shown in FIG. 3, the spacing G may be in the range of 1-6 mm, e.g, 5.3 mm.

1.3 Hollow Body and Nozzle Flexibility

The hollow body 18, e.g., formed of silicone, is relatively flexible. This flexibility allows the hollow body 18 to bend or flex which allows adjustment of the nozzles 20 attached thereto, e.g., angle nozzles 20 with respect the patient's nose in use. The nozzles 20, e.g., formed of silicone, are also relatively flexible to properly position the nozzles 20 with the nasal passages of the patient.

The hollow body 18 may also be rotatable relative to the headgear to adjust a position of the nozzles in use. Rotation of the hollow body 18 may improve seal and comfort of the nozzles in the patient's nose in use.

1.4 Child or Pre-Adult Sizing

The hollow body 18 and nozzles 20 are suitably shaped and sized to accommodate features of a child or pre-adult, e.g., 2-12 years old, preferably 2-3 years old. For example, FIG. 3 illustrates parameters of an embodiment of the hollow body 18 and nozzles 20. In an embodiment the hollow body 18 has a wall thickness of about 1 mm, a length F of about 35-40 mm, e.g., 38 mm, an inside diameter E of about 6 mm, and an outside diameter D of about 8 mm. Each nozzle 20 has a wall thickness of about 0.5 mm, an inside diameter B at the conical tip outlet opening of about 4 mm, an inside diameter C at the tube portion of about 5 mm, and an outside diameter A at the widened portion of about 10 mm. Although specific dimensions and ranges are provided for an embodiment of the hollow body 18 and nozzles 20, it is to be understood that these dimensions and ranges are merely exemplary and other dimensions and ranges are possible depending on application.

2. Headgear

Figure 6:
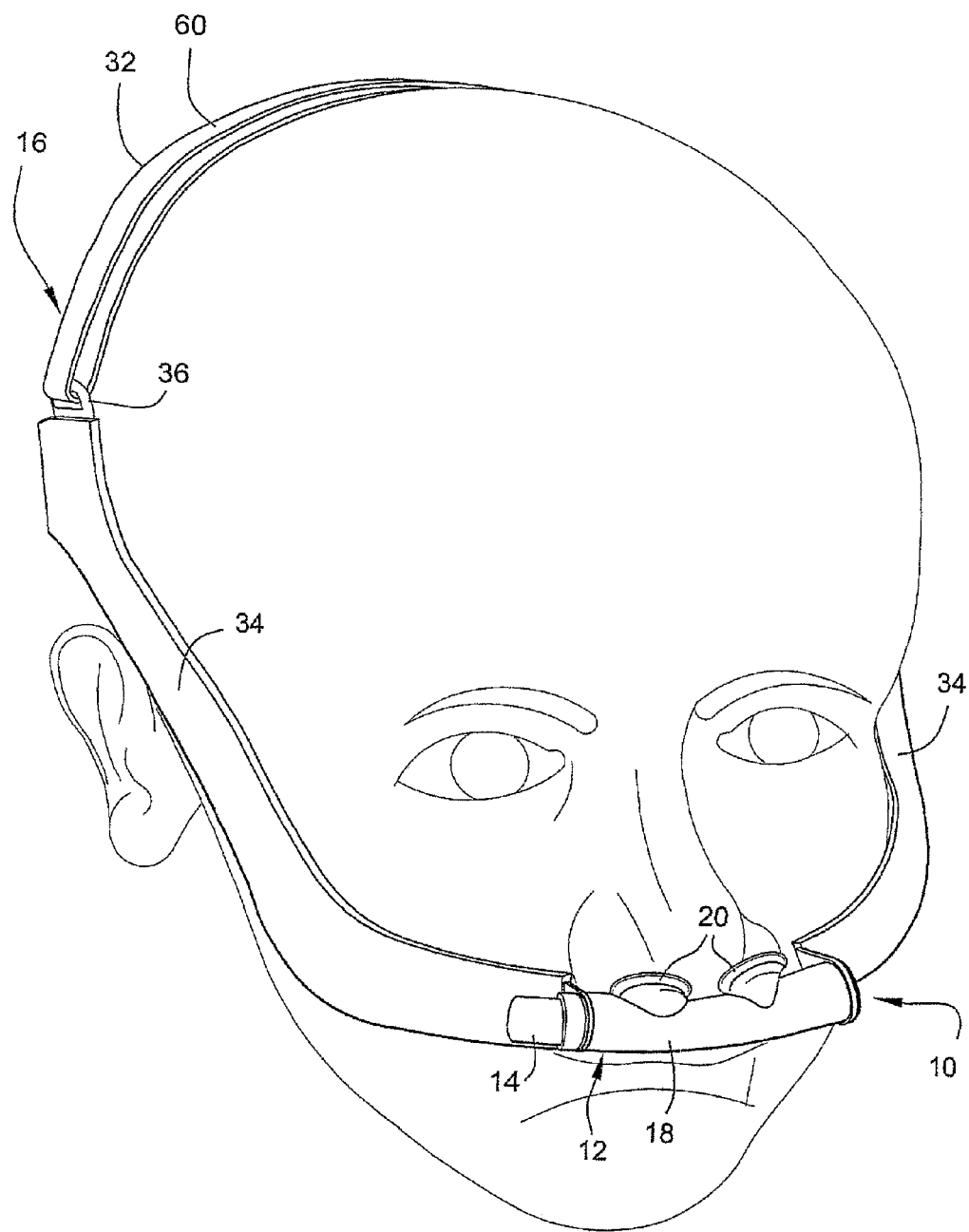
FIG. 6 is a front perspective view of the nasal assembly shown in FIG. 1 mounted to a patient's face.
Figure 7:
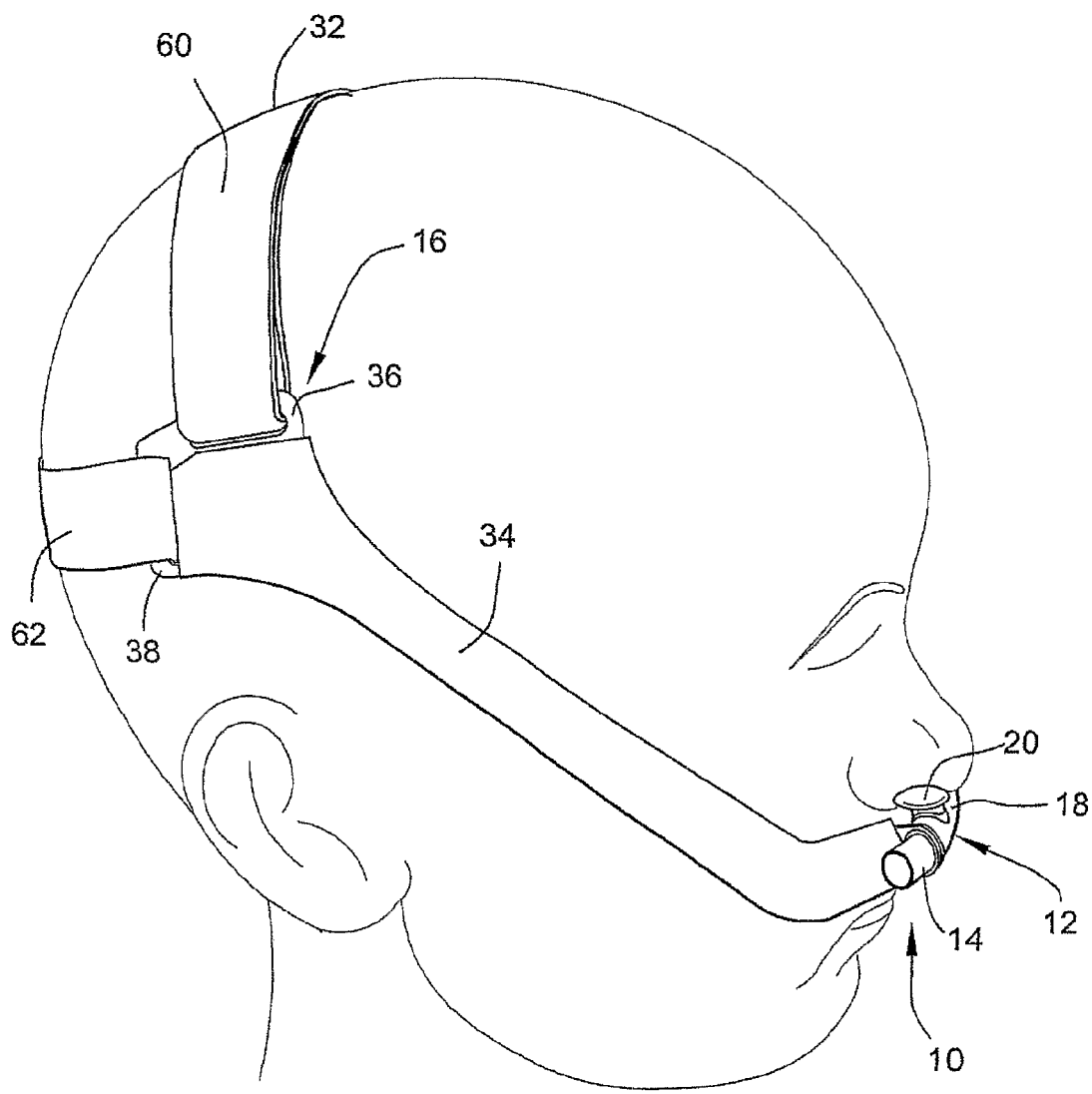
FIG. 7 is a side view of the nasal assembly shown in FIG. 1 mounted to a patient's face.

As best shown in FIGS. 1, 6, and 7, the headgear 16 includes headgear straps 32 and headgear yokes 34 provided between the headgear straps 32 and the patient interface 12.

2.1 Headgear Yokes

As shown in FIGS. 6 and 7, the yokes 34 extend from respective ends of the hollow body 18 to above the patient's ears where they engage the headgear straps 32. The yokes 34 provide a stable connection between the headgear straps 32 and the hollow body 18 in order to secure the patient interface 12 at the correct orientation on the patient's face.

The yokes 34 are relatively rigid elements that are each constructed from a rigid or semi-rigid material. In the illustrated embodiment, the yokes 34 are manufactured of a relatively rigid or stiff plastic or metal material, e.g., polycarbonate or nylon, having a thickness of 0.8 mm. However, other materials of greater or less rigidity are also possible. Also, the yokes 34 may be constructed from multiple layers, e.g., two or more layers (one of which may be silicone based, for comfort), or may be constructed from a single layer of substantially rigid material. In general, the yokes 34 are constructed of a material that will retain its shape in use.

The inside surface of each yoke 34, i.e., the surface facing the patient's face in use, may be lined with foam. In an embodiment, the entire yoke 34 may be wrapped in foam. The foam provides a soft contact surface for contacting the patient's face. In an embodiment, the foam may be a nitrogen blow medical grade open celled foam, e.g., polyether block amide (PEBA) Foam 0.8 mm manufactured by ALVEO.

In an alternative embodiment, the yokes may be provided by a bendable wire covered with cloth, foam, leather, etc. The bendable wire may be bent or adjusted to correspond with the facial contour of the patient.

2.1.1 Yoke Shape and Sizing

Each yoke 34 includes upper and lower ladder locks 36, 38 at one end for attachment to the headgear straps 32 (e.g., see FIG. 7), and a yoke ring 40 at the opposite end for attachment to the hollow body 18 (e.g., see FIGS. 2-6 and 9).

As illustrated, each yoke 34 has a bent or curved configuration along its length. Specifically, each yoke 34 has an approximate right angle bend (as indicated by arrow A.1) from the yoke ring 40 so that a portion 42 of each yoke 34 extends generally parallel with a longitudinal axis of the hollow body 18, as best shown in FIG. 4. Then, each yoke 34 is curved from the bent portion 42 so that it will curve around the patient's cheeks in use. As shown in FIG. 4, each of the yokes 34 makes an angle of about 120° with respect to the longitudinal axis of the hollow body 18. Preferably, the yokes 34 are spaced from the patient's cheeks in use, and only the conical tips 28 and a central portion of the hollow body 18 contact the patient's face in use. That is, the yokes 34 are contoured such that the yokes 34 do not contact the patient's face from the yoke ring 40 to the line B-B adjacent the patient's ears in use (see FIG. 1). However, one or more portions of the yokes 34 could potentially contact the patient's face if extra support were needed.

Figure 8:
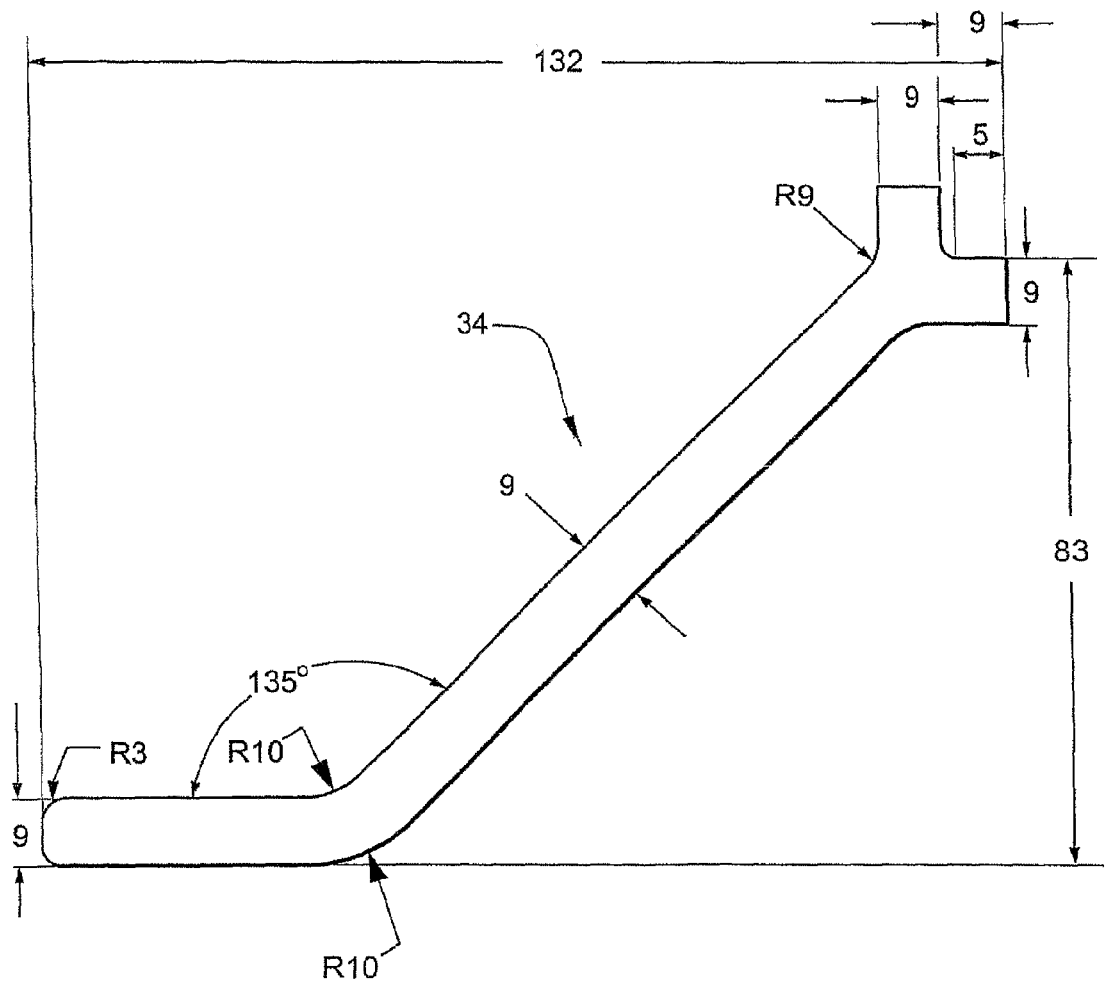
FIG. 8 is a plan view of a yoke of the headgear of the nasal assembly shown in FIG. 1 and showing exemplary dimensions of an embodiment.
Figure 9:
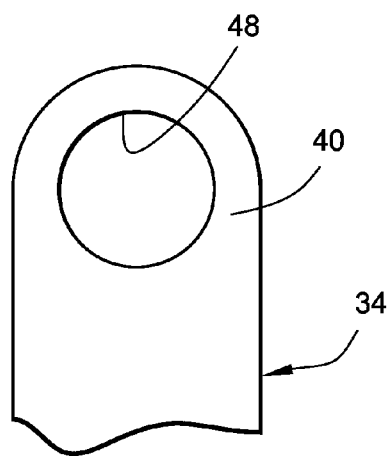
FIG. 9 is a plan view of a yoke ring of the yoke shown in FIG. 8.

The yokes 34 are suitably shaped and sized to accommodate features of a child or pre-adult, e.g., 2-12 years old, preferably 2-3 years old. For example, FIG. 8 illustrates exemplary dimensions of an embodiment of a yoke 34. Although specific dimensions of the yoke 34 are shown in FIG. 8, it is to be understood that these dimensions are merely exemplary and other dimensions are possible depending on application.

2.1.2 Yoke Connection to Patient Interface

The plug 22 and connector 24 are adapted to connect the yokes 34 to the hollow body 18. As best shown in FIG. 3, the plug 22 includes a tube portion 44 and a head portion 46. The plug 22 is engaged with one yoke 34 by inserting the tube portion 44 through the opening 48 (e.g., see FIG. 9) in the yoke ring 40. The plug 22 is then engaged with an end of the hollow body 18 by inserting the tube portion 44 into an end of the hollow body 18 such that the protrusion 50 provided on the tube portion 44 interacts with a groove 52 provided in the hollow body 18 for sealing and/or locking purposes. Moreover, the head portion 46 of the plug 22 and the end of the hollow body 18 sandwich the yoke ring 40 therebetween to secure the yoke ring 40 to the hollow body 18.

Similarly, the connector 24 includes a first tube portion 54, a flange 56, and a second tube portion 58. The connector 24 is engaged with the other yoke 34 by inserting the first tube portion 54 through the opening 48 in the yoke ring 40. The connector 24 is then engaged with the other end of the hollow body 18 by inserting the first tube portion 54 into the other end of the hollow body 18. The first tube portion 54 may be retained to the other end of the hollow body 18, e.g., by friction fit, adhesive, mechanical interlock, etc. Moreover, the flange 56 of the connector 24 and the other end of the hollow body 18 sandwich the yoke ring 40 therebetween to secure the yoke ring 40 to the hollow body 18. The second tube portion 58 is adapted to connect to the air delivery connecting member 14, e.g., by friction fit, adhesive, mechanical interlock, etc.

In use, the yoke rings 40 may rotate on the respective plug 22/connector 24 to adjust the position of the yokes 34 with respect to the hollow body 18. Also, as noted above, the positions of the plug 22 and connector 24 may be interchanged according to preference.

2.2 Headgear Straps

As best shown in FIGS. 1 and 7, the straps 32 include an upper strap portion 60 provided between the upper ladder locks 36 of the yokes 34, and a lower strap portion 62 provided between the lower ladder locks 38 of the yokes 34. In use, the upper strap portion 60 extends over the top of the patient's head and the lower strap portion 62 extends around the back of the patient's head.

The strap portions 60, 62 may be connected to respective ladder locks 36, 38 in any suitable manner, e.g., wrapped around respective ladder locks 36, 38 in a known manner. Fastening of the strap portions 60, 62 may be provided by a hook and loop material, e.g., Velcro®. However, other adjustment arrangements are possible.

3.0 Connecting Member and Air Delivery Tubing

Figure 10:
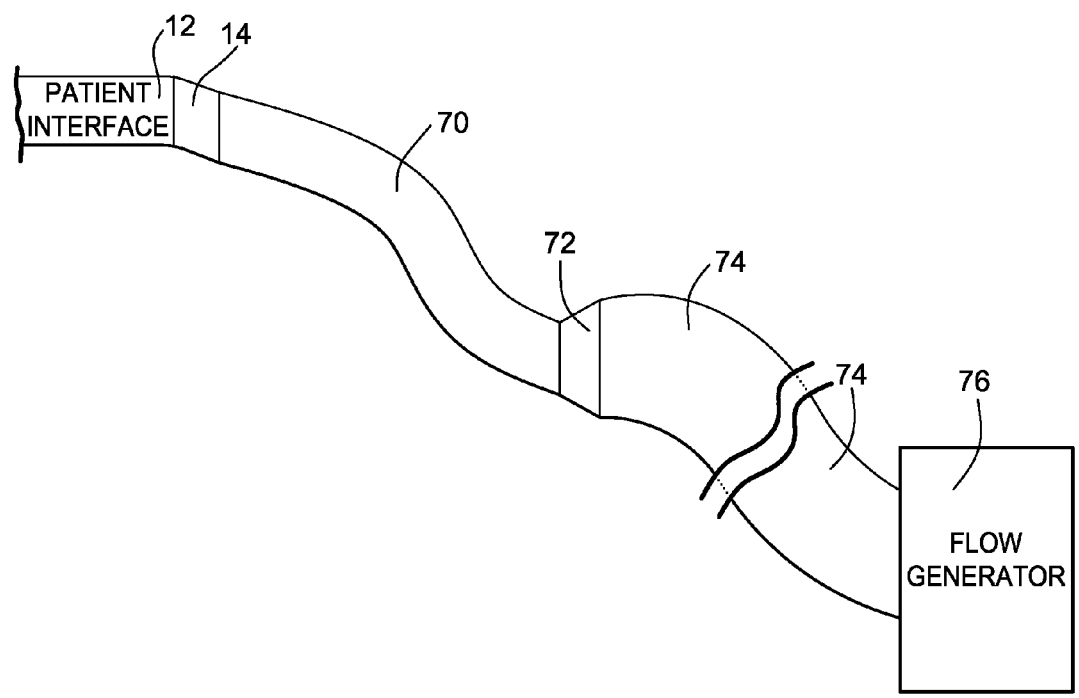
FIG. 10 is a schematic view of a breathing system including the nasal assembly shown in FIG. 1

As schematically shown in FIG. 10, a small bore tube 70 is connected to the patient interface 12 via the air delivery connecting member 14. The air delivery connecting member 14 may be an elbow that provides an angle, e.g., in the range of 5-90°. However, the air delivery connecting member 14 may be a straight connecting tube. The small bore tube 70 is communicated, e.g., via a connector 72, with a larger bore tube 74 associated with the flow generator 76. In use, the flow generator 76 provides pressurized air, e.g., in the range of 4-10 cmH$_2$O, to the patient interface via the tubes 70, 74.

In the illustrated embodiment, the small bore tube 70 has substantially the same diameter as the hollow body 18 of the patient interface 12, e.g., 6 mm inside diameter. The small bore tube 70 may have a length of 15-25 mm, e.g., 24 mm. The larger bore tube 74, e.g., 22 mm inside diameter, may have a length of 20-30 mm, e.g., 20 mm.

4.0 Children or Pre-Adult Use of Nasal Assembly

The nasal assembly 10 includes several features that facilitate use for children or pre-adults. For example, the nasal assembly 10 is structured such that only the conical tips 28 and a central portion of the hollow body 18 may contact the patient's face in use. That is, the patient interface 12 contacts the patient's face at the nose and below the nose only. This arrangement makes the nasal assembly 10 non-obtrusive so it doesn't apply pressure to regions of the patient's face that may lead to discomfort.

Another feature is the circular configuration of the nozzles 20. This arrangement more closely follows the shape of children's nasal passages which are more circular than elliptical for example.

Yet another feature is the flexibility of the hollow body 18 which facilitates adjustment of the nozzles 20.

Still another feature is that the parameters of the patient interface 12 and headgear 16 are sized and/or shaped to accommodate features of a child or pre-adult. In addition, the smaller bore air delivery tube 70, e.g., 6 mm vs. larger 15 mm provided in known nasal assemblies, provides air pressure at a level suitable for children or pre-adults, e.g., 4-10 cmH$_2$O.

The nasal assembly provides an interface having comfort and softness, stability, and unobtrusiveness. In an embodiment, comfort and softness may be enhanced by including a textile sock or covering around at least a portion of the assembly and/or a yoke constructed of or covered with a silicone material. In an embodiment, stability may be enhanced by including headgear having a bonnet design, e.g., headgear formed with a cupping portion at the back to better grip the occipital region of the child's head. In the illustrated embodiment, the nasal assembly is unobtrusive because it does not cover the eyes of a child or pre-adult. In an embodiment, unobtrusiveness may be enhanced by providing an air delivery connecting member or inlet tube that is integral with the above-noted silicone yoke, that extends up to a manifold provided at the top/back of a patient's head, that is collapsible (such as collapsible conduit headgear described in PCT Publication No. WO 2005/099801, published Oct. 27, 2005, the entirety of which is incorporated herein by reference), that is not collapsible, that is unattached to the headgear except where it meets the patient interface, and/or that is attached to the headgear at any point along the headgear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from obstructive sleep apnea (OSA), it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A nasal assembly, comprising:
   a patient interface including a hollow body that defines an air chamber and a pair of nozzles supported by the hollow body, each nozzle including a conical tip structured to sealingly communicate with a respective nasal passage of a patient's nose in use; and headgear provided to the patient interface so as to maintain the patient interface in a desired position on the patient's face in use, the headgear structured to not extend across or be supported by a patient's forehead, wherein the hollow body is bendable to adjust a position of the nozzles in use, wherein the hollow body is in the form of a silicone cylindrical tube including at least one silicone cylindrical end portion structured to support a plug or a connector that supports an air delivery connecting member, wherein the headgear includes headgear straps and relatively rigid headgear yokes provided between the headgear straps and the patient interface, the headgear yokes being configured such that the headgear yokes are spaced from the patient's cheeks in use, and only the conical tip of each nozzle and a central portion of the hollow body are adapted to contact the patient's face in use, wherein the headgear yokes are contoured such that each headgear yoke is adapted to be spaced from the patient's cheek by a space to prevent contact with the patient's cheek in use, the space configured to extend from a connection of each headgear yoke to the patient interface to a portion of each headgear yoke adapted to be positioned generally above and adjacent with respect to the patient's ears in use.

2. The nasal assembly according to claim 1, wherein the patient interface and headgear are sized and shaped for children or pre-adults in the range of 2-12 years old.

3. The nasal assembly according to claim 1, wherein the patient interface and headgear are sized and shaped for children or pre-adults in the range of 2-3 years old.

4. The nasal assembly according to claim 1, wherein the nozzles are formed of silicone.

5. The nasal assembly according to claim 1, wherein the hollow body and nozzles are formed separately from one another and then attached to one another.

6. The nasal assembly according to claim 1, wherein each nozzle includes a cylindrical tube provided to the hollow body that supports the conical tip.

7. The nasal assembly according to claim 1, wherein the conical tip includes an outlet opening, the outlet opening having a circular shape.

8. The nasal assembly according to claim 7, wherein the outlet opening has an inside diameter of about 4 mm.

9. The nasal assembly according to claim 1, wherein the conical tip includes a widened portion having an outside diameter of about 10 mm.

10. The nasal assembly according to claim 1, wherein the hollow body has an inside diameter of about 6 mm.

11. The nasal assembly according to claim 1, wherein each end of the silicone cylindrical tube includes a cylindrical end portion, one of the end portions is provided with the plug and the other of the end portions is provided with the connector.

12. The nasal assembly according to claim 11, wherein positions of the plug and connector may be interchanged.

13. The nasal assembly according to claim 1, wherein the yokes are constructed from rigid or semi-rigid material.

14. The nasal assembly according to claim 1, wherein the yokes are constructed from polycarbonate.

15. The nasal assembly according to claim 1, wherein the yokes are at least partially covered with foam.

16. The nasal assembly according to claim 1, wherein each of the yokes makes an angle of about 120° with respect to a longitudinal axis of the hollow body.

17. The nasal assembly according to a claim 1, wherein each of the yokes includes a yoke ring for attachment to the hollow body.

18. The nasal assembly according to claim 17, wherein the yoke ring of one yoke is sandwiched between the plug and an end of the hollow body.

19. The nasal assembly according to claim 18, wherein the yoke ring of the other yoke is sandwiched between the connector and the other end of the hollow body.

20. The nasal assembly according to claim 1, wherein the headgear straps include an upper strap portion adapted to extend over the top of the patient's head and a lower strap portion adapted to extend around the back of the patient's head.

21. The nasal assembly according to claim 20, wherein the upper and lower strap portions are connected to the yokes via a ladder lock arrangement.

22. The nasal assembly according to claim 1, wherein the patient interface is adapted to contact the patient's face only at the nose and below the nose.

23. The nasal assembly according to claim 1, wherein the hollow body is rotatable relative to the headgear to adjust a position of the nozzles in use.

24. A breathing system, comprising: a flow generator; air delivery tubing; and a nasal assembly according to claim 1.

25. The breathing system according to claim 24, wherein the air delivery tubing includes a first delivery tube coupled to the hollow body or tubular air chamber, the first delivery tube having an inside diameter that is substantially the same as an inside diameter, of the hollow body or tubular air chamber.

26. The breathing system according to claim 25, wherein the hollow body or tubular air chamber have an inside diameter of about 6 mm.

27. The breathing system according to claim 24, wherein the air delivery tubing includes a second delivery tube coupled between the first delivery tube and the flow generator, the second delivery tube having an inside diameter that is larger than the inside diameter of the first delivery tube.

28. The breathing system according to claim 27, wherein the second delivery tube has an inside diameter of about 22 mm.

29. The breathing system according to claim 24, wherein in use the flow generator provides pressurized air in the range of 4-10 cmH$_2$O to the patient.

30. The nasal assembly according to claim 1, wherein the hollow body and the pair of nozzles are formed as a one-piece structure such that the hollow body is integrally formed in one-piece along with the nozzles.

31. The nasal assembly according to claim 1, wherein each of the at least one silicone cylindrical end portion provides a substantially continuous interior cylindrical surface to engage and support the plug or connector.

32. The nasal assembly according to claim 1, wherein each conical tip includes a concave outer surface such that each conical tip tapers from its base towards its distal end whereby a width of the distal end is less than a width of the base, and the conical tip is adapted to seal around the patient's nare along the concave outer surface.

33. The nasal assembly according to claim 1, wherein the hollow body is not supported by a relatively rigid frame.

34. The nasal assembly according to claim 1, wherein each end of the silicone cylindrical tube includes a cylindrical end portion.

35. The nasal assembly according to 1, wherein the portion is adjacent an end portion of each yoke that provides a ladder lock arrangement structured to connect to the headgear straps.

* * * * *

UNITED STATES PATENT AND TRADEMARK OFFICE
CERTIFICATE OF CORRECTION

PATENT NO. : 8,701,668 B2  
APPLICATION NO. : 11/988928  
DATED : April 22, 2014  
INVENTOR(S) : Selvarajan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1830 days.

Signed and Sealed this

Twenty-ninth Day of September, 2015

Michelle K. Lee
*Director of the United States Patent and Trademark Office*